United States Patent
Motoi (10) Patent No.: US 7,531,797 B2
(45) Date of Patent: May 12, 2009

(54) PROBE-HOLDING APPARATUS, SAMPLE-OBTAINING APPARATUS, SAMPLE-PROCESSING APPARATUS, SAMPLE-PROCESSING METHOD AND SAMPLE-EVALUATING METHOD

(75) Inventor: Taiko Motoi, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/029,766

(22) Filed: Feb. 12, 2008

(65) Prior Publication Data

US 2008/0135752 A1    Jun. 12, 2008

Related U.S. Application Data

(63) Continuation of application No. 10/541,551, filed on Jul. 6, 2005, now Pat. No. 7,385,206.

(51) Int. Cl.
*H01J 37/08* (2006.01)
(52) U.S. Cl. ............. 250/309; 250/492.21; 250/442.11; 250/443.1; 250/306
(58) Field of Classification Search ............ 250/492.21, 250/306, 309, 442.11, 443.1
See application file for complete search history.

(56) References Cited

U.S. PATENT DOCUMENTS

| | | | |
|---|---|---|---|
| 3,978,686 A | | 9/1976 | Lechner et al. ........... 62/514 R |
| 4,747,698 A | * | 5/1988 | Wickramasinghe et al. .... 374/6 |
| 4,916,314 A | | 4/1990 | Smith ........................ 250/307 |
| 4,983,830 A | * | 1/1991 | Iwasaki ...................... 250/309 |
| 5,047,637 A | * | 9/1991 | Toda .......................... 250/306 |
| 5,182,253 A | | 1/1993 | Kishi et al. ..................... 505/1 |
| 5,270,552 A | | 12/1993 | Ohnishi et al. ............. 250/307 |
| 5,440,122 A | * | 8/1995 | Yasutake ................ 250/443.1 |
| 6,344,115 B1 | * | 2/2002 | Azuma et al. .......... 204/192.34 |
| 6,538,254 B1 | | 3/2003 | Tomimatsu et al. .... 250/442.11 |
| 6,744,268 B2 | * | 6/2004 | Hollman ...................... 324/758 |
| 6,858,851 B2 | * | 2/2005 | Tomimatsu et al. .... 250/442.11 |

(Continued)

FOREIGN PATENT DOCUMENTS

JP        47-005118        9/1972

(Continued)

OTHER PUBLICATIONS

S.L. Peterson, et al., "Inexpensive Ultrahigh Vacuum Heatable/Coolable XYZ-Rotary Motion Sample Manipulator," Review of Scientific Instruments, American Institute of Physics, vol. 66, No. 4, pp. 3048-3050 (Apr. 1, 1995).

(Continued)

*Primary Examiner*—Jack I Berman
*Assistant Examiner*—Michael J Logie
(74) *Attorney, Agent, or Firm*—Fitzpatrick, Cella, Harper & Scinto (57) ABSTRACT

A sample processing apparatus includes a stage for supporting a sample, a first temperature controller for controlling a temperature of the sample, an ion beam generator for irradiating the sample with an ion beam, and a detector for detecting a signal emitted from the sample in response to the irradiation of the ion beam. Also provided is a probe for obtaining a part of the sample processed by the irradiation of the ion beam and conveying it to a sample table, a second temperature controller for controlling a temperature of the probe, and a third temperature controller for controlling a temperature of the sample table.

9 Claims, 7 Drawing Sheets

U.S. PATENT DOCUMENTS

| | | | |
|---|---|---|---|
| 2001/0017060 A1 | 8/2001 | Offen et al. | 73/863.11 |
| 2001/0045511 A1* | 11/2001 | Moore et al. | 250/221 |
| 2002/0014013 A1 | 2/2002 | Graupner et al. | 30/350 |
| 2002/0050565 A1 | 5/2002 | Tokuda et al. | 250/310 |
| 2003/0151421 A1* | 8/2003 | Leedy | 324/760 |
| 2004/0173457 A1 | 9/2004 | Miller et al. | 204/451 |
| 2005/0166845 A1* | 8/2005 | Cox | 118/725 |

FOREIGN PATENT DOCUMENTS

| | | |
|---|---|---|
| JP | 58-005505 | 1/1983 |
| JP | 59-221955 | 12/1984 |
| JP | 5-52721 | 3/1993 |
| JP | 05028946 | 3/1994 |
| JP | 09-161707 | 6/1997 |
| JP | 09306405 | 11/1997 |
| JP | 2000-217290 | 8/2000 |
| JP | 2001-345360 | 12/2001 |
| JP | 2002-082024 | 3/2002 |
| JP | 2002-334677 | 11/2002 |
| JP | 2004-286699 | 10/2004 |

OTHER PUBLICATIONS

PCT International Search Report dated Apr. 5, 2004, issued in corresponding PCT Patent Application No. PCT/JP2004/000502, mailed May 21, 2004.

* cited by examiner

PROBE-HOLDING APPARATUS, SAMPLE-OBTAINING APPARATUS, SAMPLE-PROCESSING APPARATUS, SAMPLE-PROCESSING METHOD AND SAMPLE-EVALUATING METHOD

This is a continuation of application Ser. No. 10/541,551, filed on Jul. 6, 2005.

TECHNICAL FIELD

The present invention relates to an apparatus for preparing a specimen. More particularly, it relates to an apparatus for isolating and obtaining a part of a sample of which state and shape may be changed with temperature change. It also relates to a sample-processing apparatus for preparing a specimen, and a method for evaluating the prepared specimen.

BACKGROUND ART

With the increase of functional devices, demand for cross-sectional evaluation or fine processing of organic substances such as biological materials and plastics is increasing. Methods for making cross sections of organic materials in order to obtain structural information include cutting with a knife, resin embedding, freeze-embedding, freeze-fracture and ion etching. Usually, for internal structure observation of an organic matter by optical microscopy, the sample is embedded in a resin and sliced with a microtome.

However, the optical microscope allows only macroscopic observation of the cross section and the cut-out position cannot be designated in this method, so that it requires an enormous amount of repeating work of preparing cross sections in order to observe and analyze the structure at a desired position.

Recently, focused ion beam (FIB) techniques that can process a predetermined site have been developed, where a finely focused ion beam from an ion source irradiates a sample for processing it by etching etc. Such FIB etching has become considerably popular, and utilized widely for structural analysis or failure analysis of semiconductors or the like, and for sample preparation of scanning electron microscopy (SEM), transmission electron microscopy (TEM) etc.

Recently, several methods have been proposed to cut out a portion of a sample and process it applying manipulation techniques to FIB techniques. For example, Japanese Patent Application Laid-Open No. H05-52721 proposes a method of cutting out a part of a sample by FIB and the cut out minute sample is held on a probe, which facilitates isolation of only the necessary portion for analysis.

Japanese Patent Application Laid-Open No. 2001-345360 proposes a method of cutting out a minute specimen by using an ion beam and then bombarding it with another ion beam to reduce the influence of the element of the first ion beam employed for cutting out.

However, when the sample is a material of which state and shape will change with temperature such as an organic substance, it is difficult to prepare a minute specimen of a desired shape using such a probe since the temperature of such a probe often becomes higher than that of the sample resulting in heating of the contacted part of the sample.

Thus, the present invention is to provide an apparatus for conveying a sample for observation without heat-denaturation.

The present invention is also to provide an apparatus suitable for obtaining a necessary minute piece from a sample.

The present invention is also to provide a sample processing apparatus capable of efficiently processing a necessary minute piece from a sample under temperature control of the sample.

Furthermore, the present invention is to provide a sample evaluating apparatus and a sample evaluating method for analysis of a cross section structure under temperature control of the sample.

Furthermore, the present invention is to provide a sample-conveying apparatus capable of conveying a sample for electron microscopic observation under temperature control of the sample.

DISCLOSURE OF THE INVENTION

The sample-conveying apparatus of the present invention comprises a probe for conveying a specimen to be observed, and temperature control means for controlling a temperature of the probe whereby the sample does not change during conveyance.

The specimen-obtaining apparatus of the present invention comprises a stage for supporting a sample; first temperature control means which controls a temperature of the sample; means for isolating a part of the sample; probe moving means for mounting and moving a probe; a probe for obtaining a part of the sample isolated by the isolation means; and second temperature control means for controlling a temperature of the probe.

The sample-processing apparatus of the present invention comprises a stage for supporting a sample; first temperature control means for controlling a temperature of the sample; ion beam generation means for irradiating the sample with an ion beam; detection means for detecting a signal emitted from the sample in response to the irradiation of the ion beam; a probe for obtaining a part of the sample processed by the irradiation of the ion beam; a sample table for evaluation; second temperature control means for controlling a temperature of the probe; and third temperature control means for controlling a temperature of the sample table.

The sample evaluation apparatus of the present invention is characterized in that ion beam irradiation is carried out by using ion beam generating means and information is acquired by the detection means with a sample preconditioned at the predetermined temperature by temperature-controlling means, the sample is cut out and pasted under the conditions the temperature of the probe and the sample has been adjusted at a predetermined temperature by temperature-controlling means.

According to preferred embodiments, a sample table for evaluation may be provided separately from the stage. Also the temperature control means may be provided with cooling means which cools the sample to a temperature equal to or less than the room temperature. The stage, the ion beam generation means, the ion beam detection means, the probe and the sample table may be provided within a chamber with a controllable atmosphere, and there may be further provided trap means for trapping gas remaining in the chamber.

Also the emission signal may be secondary electrons or secondary ions. Also the detection means may be constituted of a first detector for detecting secondary electrons and a second detector for detecting secondary ions.

As described above, according to the present invention, temperature of the probe is regulated by the second temperature control means to maintain the temperature of the sample at a desired temperature, so that a minute specimen can be obtained from a sample of which state and shape are susceptible to temperature change. Also the first temperature control means allows to maintain the sample at a desired temperature during sample processing, for example, FIB operation. Furthermore, since the sample table for evaluation can be temperature-controlled by the third temperature control means, the sample after fixation to the sample table can be maintained at a desired temperature. Consequently, change in state or shape of the sample would not occur as in the prior technology.

The sample processing method of the present invention comprises the steps of regulating temperature of a sample, a probe and a sample table; sectioning or processing the sample by irradiating a predetermined portion of the sample with an ion beam from at least two angular directions relative to a surface of the sample; and connecting the probe to a part of the sectioned sample.

The sample-evaluation method of the present invention comprises the steps of regulating a temperature of a sample, a probe and a sample table; sectioning or processing the sample by irradiating a predetermined portion of the sample with an ion beam from at least two angular directions relative to a surface of the sample; connecting the probe to a part of the sectioned sample; isolating the sectioned sample to which the probe has been attached; attaching the isolated sample to the sample table using the probe; cutting off the probe; and irradiating the sample attached to the sample table with an evaluation beam for evaluation to obtain from an emitted signal an image of a cross-sectioned face of the sample generated by the sectioning or processing step.

The present invention also provides a conveying apparatus which comprises a conveying member for conveying a sample for observation under an electron microscope; and temperature regulation means which regulates a temperature of the conveying member; wherein the temperature regulation means regulates the temperature of the sample in such a manner that it does not change before and after the conveyance.

BEST MODE FOR CARRYING OUT THE INVENTION

Now embodiments of the present invention will be explained with reference to accompanying drawings.

Embodiment 1

Figure 1:
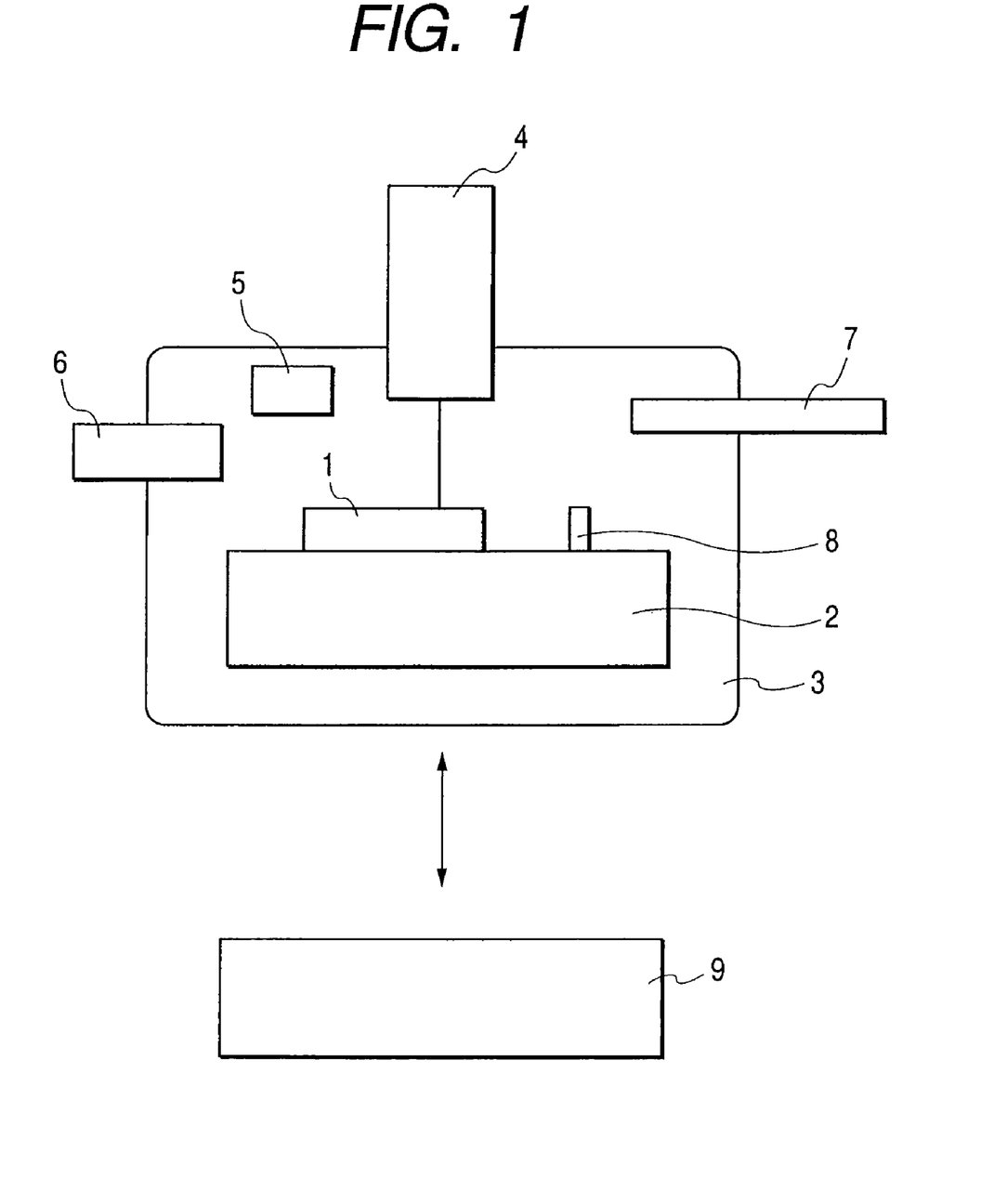
FIG. 1 is a schematic view of a focused ion beam processing apparatus being an embodiment of the sample processing apparatus of the present invention.

FIG. 1 is a-schematic view of a focused ion beam processing apparatus constituting a first embodiment of the sample-processing apparatus of the present invention.

The processing apparatus is provided with a temperature holding unit 2 on which a sample 1 is fixed and which maintains the fixed sample 1 at a predetermined temperature. The temperature holding unit 2 can be accommodated in a sample chamber 3.

The sample chamber 3 is provided with an ion beam generating unit 4 for irradiating the sample 1, fixed to the temperature holding unit 2, with an ion beam, an electron detector 5 for detecting secondary electrons emitted from the sample 1 by the ion beam irradiation, gas introducing means which enables a film deposition on the sample 1 by the ion beam irradiation, and a probe-holding unit 7 capable of mounting a probe (not shown) for fixing a part of the sample cut out by the ion beam irradiation. The probe-holding unit 7 is preferably a manipulator that serves as probe-moving means for moving the tip of the probe three-dimensionally. There is also provided a sample table 8 for facilitating evaluation with another analysis apparatus.

The interior of the sample chamber 3 can be evacuated by a pump (not shown) and can be maintained at a predetermined low pressure, thereby enabling an ion beam irradiation. The interior of the sample chamber 3 is preferably maintained at a pressure within a range from $10^{-10}$ to $10^{-2}$ Pa.

The ion beam generation unit 4 is used as means for isolating a part of the sample by irradiating the sample 1 with the ion beam, and also as processing means for processing the sample, for example, to reveal a cross-section of the sample. It can also be used for scanning ion microscopy (SIM) observation. In case of SIM observation, the ion beam generation unit 4 and the electron detector 5 serve as information acquisition means, and the secondary electrons generated when the sample 1 is irradiated with the ion beam are detected by the electron detector 5 and an image is formed on the basis of detection signals from the electron detector 5.

The detection signal from the electron detector 5 is sent to a control unit 9 constituting control means for imaging, and imaging of the aforementioned SIM observation is executed by the control unit 9. For example, the control unit 9 receives image information (mapping information) in the detection signal from the electron detector 5 and displays the obtained image information as an image on an display apparatus (not shown). In addition, the control unit 9 controls ion beam generation in the ion beam generation unit 4 and controls irradiation and scanning of such ion beam onto the sample 1. The beam scanning can be controlled at the side of the unit 4, or at the side of the unit 2 on which the sample is fixed, or both, but control at the side of beam generating unit 4 is desirable in consideration of the scanning speed. Also the irradiating position of the ion beam can be so controlled as to focus it on the probe tip on the sample 1.

The ion beam generation unit 4 may have such a configuration as described in Japanese Patent Application Laid-Open No. H05-52721 or No. 2000-217290.

Probe

The probe in the present embodiment is used for obtaining a sample piece (specimen) from a sample by fixing the piece to the probe tip (not shown), and the sample piece is separated from the sample by processing.

Also the probe tip is preferably constituted of a material of a satisfactory thermal conductivity, in consideration of temperature control. Also the material preferably has a certain resistance to the ion beam, since SIM imaging with the FIB is used for confirming the position of the sample or the probe. Furthermore, the probe tip is consumed, cut off little by little after the specimen is attached to the sample table. For this reason, it is preferable that the probe or at least the probe tip can be replaced.

Configuration of the First, Second and Third Temperature Control Means

Figure 2:
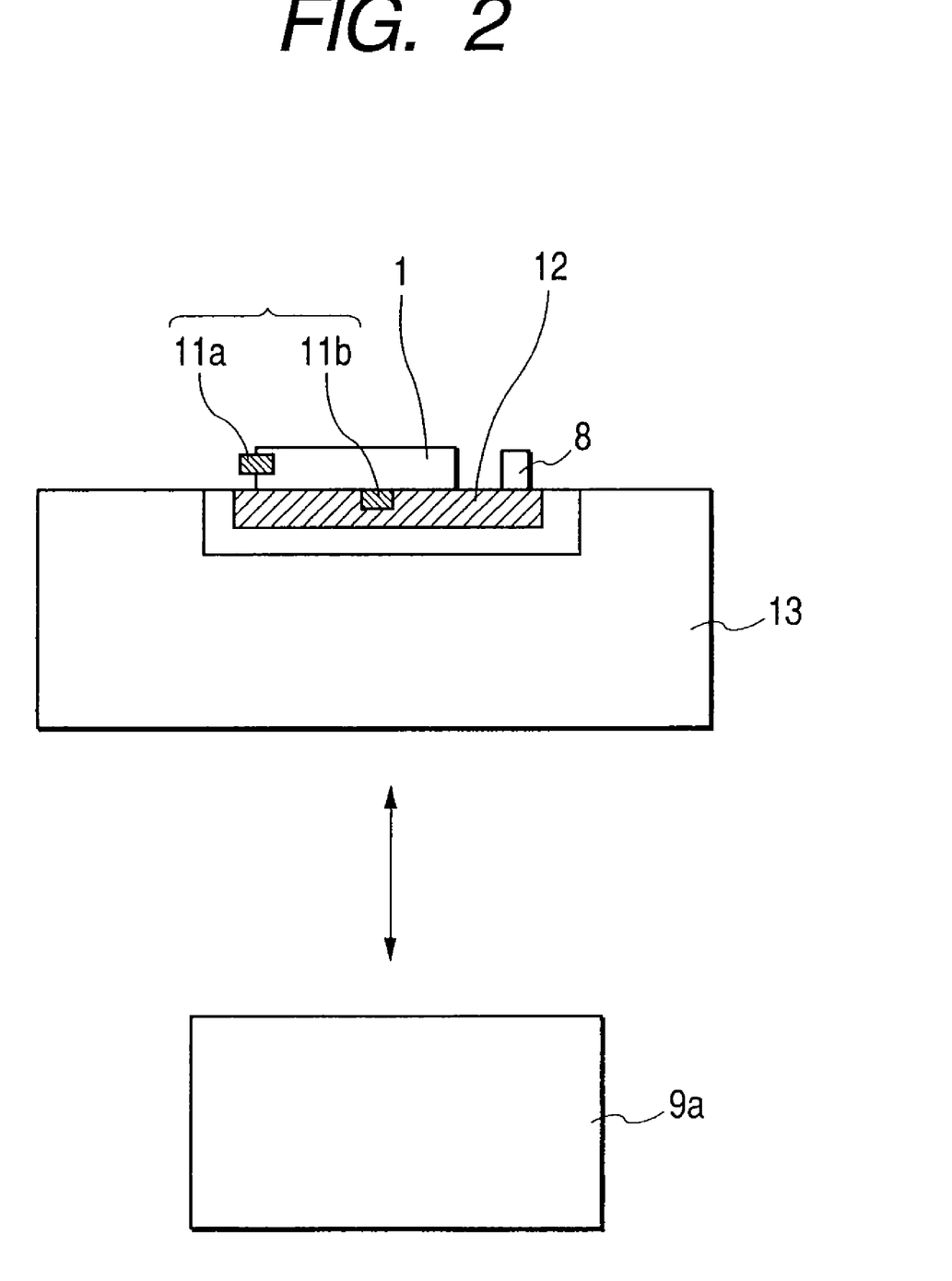
FIG. 2 is a block diagram showing a schematic configuration of a sample stage with a temperature controller, an example of a temperature-holding unit shown in FIG. 1.

In the present embodiment, the first temperature control means is provided with a temperature holding unit 2 capable of temperature control of the sample. The temperature holding unit 2 is, for example, a sample stage provided with a temperature controller. FIG. 2 schematically shows a configuration of such a sample stage with a temperature controller.

Referring to FIG. 2, the sample stage with the temperature controller is constituted of a sample stage 13 having a temperature-varying system 12 in a portion on which the sample 1 is fixed, a thermometer 11a for directly detecting the temperature of the sample 1, a thermometer 11b attached to a part of the temperature-varying system 12 to detect the temperature in the vicinity of the sample 1 fixed to the temperature-varying system 12, and a temperature control unit 9a for controlling the temperature of the temperature-varying system 12 on the basis of the temperature detected by the thermometer 11b, thereby maintaining the sample 1 at a predetermined temperature.

Although not shown in FIG. 2, there is also provided a display unit for displaying the temperature detected by the thermometer 11b, and the operator can confirm the temperature of the sample 1 displayed on the display unit. Also the temperature control unit 9a may be so constructed as to regulate the temperature of the temperature varying system 12 according to the temperatures detected by both the thermometers 11a and 11b, and such configuration enables a more accurate temperature control of the sample 1. In the present embodiment, the sample table 8 for evaluation is also fixed to the temperature holding unit 2 like the sample 1, and can be controlled at a predetermined temperature. In such case the first temperature control means serves also as the third temperature control means, but such configuration is not restrictive and there may be provided separate temperature control means.

The temperature varying system 12 is integrated with the thermometer 11b as a unit in the sample stage 13 to control the temperature in a necessary range. Such unit can be, for example, a high temperature unit having a heating mechanism such as a heater or a low temperature unit having a cooling mechanism. It may be, if necessary, a unit having a temperature varying function ranging from low to high temperature spanning room temperature.

The sample stage 13 can mechanically move, rotate or incline the fixed sample 1 three dimensionally, and thus can move the sample 1 to a desired position for evaluation. The movement control of the sample 1 on the sample stage 13 is achieved by the aforementioned control unit 9.

The aforementioned cooling mechanism can employ, for example, a Peltier element or a helium freezer. Otherwise, the aforementioned cooling mechanism may be constructed such that a cooling pipe for a coolant is provided in the temperature holding unit beneath the area where the sample is fixed so that a coolant such as liquefied nitrogen or water thermally comes in contact with the temperature holding unit.

Also in order to increase the efficiency of heat absorption for heat generated during the processing operation, it is preferable to increase the contact efficiency between the sample and the cooling unit (temperature holding unit). Such a design can be realized, for example, by preparing a sample holder in such a configuration as to wrap up the sample but not to hinder optical systems employed in processing and in observation, or by processing the sample in such a shape as to match that of the holder so that the sample is held maintaining a maximum contact area.

Furthermore, it is also possible to cover a non-worked area of the sample with a cooling member. In such case, the cooling member is to be so placed as not to intercept the beam.

Also in this embodiment, a similar temperature holding unit may be incorporated in the probe as the second temperature control means for controlling the temperature of the probe. In such case, it may be controlled by another control unit, but it is also possible to use the control unit 9 for controlling the temperature of the sample and the probe.

Also the temperature control means for controlling the temperature of the probe may be of such a configuration that the probe is connected to the probe moving means and they are in thermal contact thereby achieving the temperature control.

Figure 7:
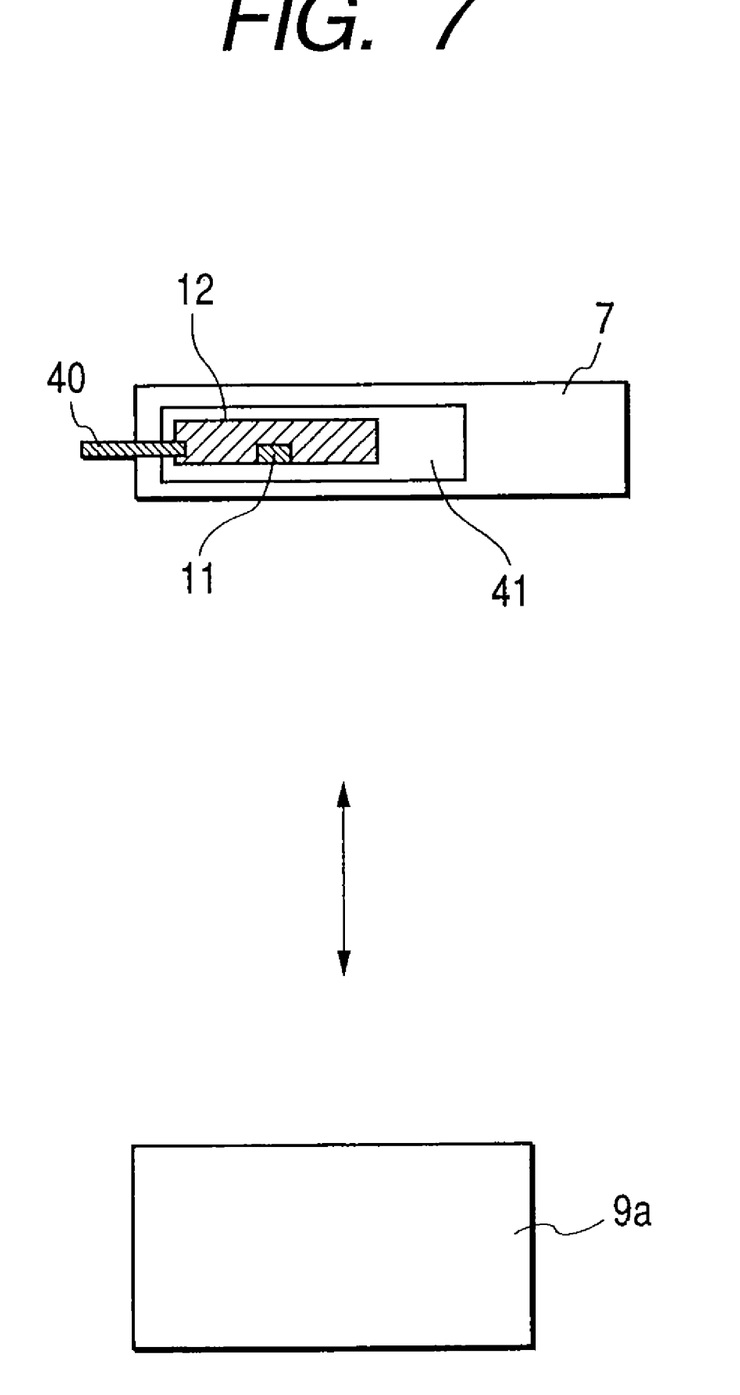
FIG. 7 is a block diagram showing a schematic configuration of probe-moving means provided with a temperature controller, an example of probe-moving means shown in FIG. 1.

Also the probe, the probe moving means and the second temperature control means may be constructed as shown in FIG. 7. Referring to FIG. 7, a probe 40 can be mounted on a probe holder 41 provided with a temperature varying system 12 having a thermometer 11. The probe holder 41 provided with the probe 40 is contained in the probe moving means. Also the probe holder 41 can move in the prove moving means 7 according to necessity for probe protection, and the tip of the probe 40 can retract in or jut from the probe moving means 7 according to the necessity.

Also the temperature of the probe may be regulated by the second temperature control means, according to the temperature of the sample regulated by the first temperature control means.

Also the first temperature control means and the second temperature control means preferably communicate electrically, and the temperature of the probe is synchronously regulated by the second temperature control means, according to the temperature of the sample regulated by the first temperature control means.

The sample and the probe are preferably maintained at substantially the same temperature by the first and second temperature control means, but there may also be employed different temperatures.

In such case, it is preferable to maintain the probe at a lower temperature.

Cross Section Evaluating Method for Sample

A cross section evaluation method of the present invention will be explained in the following.

Figure 3:
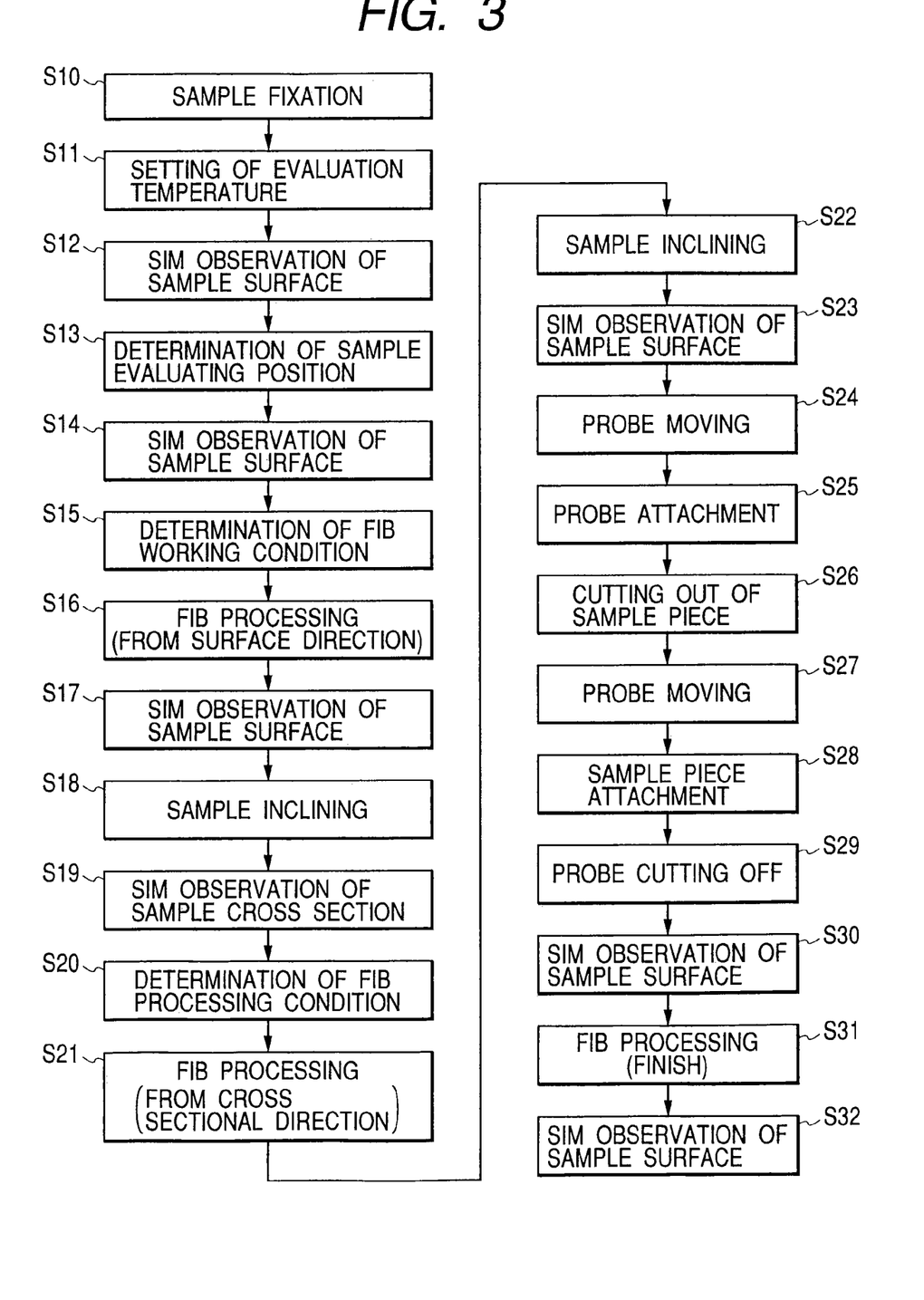
FIG. 3 is a flow chart showing a process of a cross section processing of a sample by the focused ion beam apparatus shown in FIG. 1.

FIG. 3 is a flow chart showing a process of evaluation of a cross section of the sample, utilizing the sample processing apparatus shown in FIG. 1. In the following there will be given an explanation on the process of cross sectional evaluation with reference to FIG. 3, and also on the control for FIB processing and SIM observation by the control unit 9 and the temperature control of the sample by the temperature control unit 9a according to such process.

First, the sample 1 and the sample table 8 are fixed on a predetermined position (temperature varying system 12) of the sample stage 13 (step S10), and, after an introduction thereof into the sample chamber 3, an evaluation temperature (temperature at which evaluation is carried out) is set (step S11). At the same time, the evaluation temperature of the probe is similarly set. Once the evaluation temperature is set, the temperature control unit 9a controls the temperature at the temperature varying system 12, whereby the sample 1 and the sample table 8 are maintained at such a set evaluation temperature. The temperature of the sample 1 is detected by the thermometer 11a, and the operator can confirm, by the detected temperature displayed on the display unit (not shown), whether the sample 1 is maintained at such evaluation temperature.

In the present embodiment, it is preferred to cool the sample to a temperature lower than the room temperature for processing. Also by cooling to 0° C. or lower, it is possible to solidify water present in the sample.

In case of employing such a cooling step, it is preferable to first cool the sample to the room temperature or lower, then to maintain the cooled sample in an atmosphere of a reduced pressure, and to execute the irradiation with the focused beam while absorbing the heat generated from the irradiated surface of the sample and the vicinity thereof, thereby maintaining the shape of the non-irradiated portion.

Also in sample cooling, rapid cooling from the room temperature may be adopted. In such a case, preferably the cooling rate is 40° C./min or more, whereby. In this manner, it is possible to observe a cross section in a rapidly cooled state even when the sample is a mixture of which dispersibility varies by temperature.

The cooling step is preferably executed before a pressure reducing step. In this manner it is possible to suppress evaporation of the sample under a reduced pressure. In case the sample is constituted of a substance of low evaporation, the cooling may be executed simultaneously with the pressure reduction. The probe may be cooled after the pressure reduction.

The cooling step varies depending on the sample to be processed, but, in case of an ordinary organic substance such as PET, cooling is preferably executed within a temperature range, of 0 to −200° C., more preferably −50 to −100° C.

If the processing time or the cooling time becomes too long and the sample stays in a low temperature state too long, a gas remaining in the sample chamber or a substance generated in the processing may be adsorbed on the cooled sample, rendering the desired processing or observation difficult. For this reason, it is preferable to provide trap means for adsorbing the remaining gas or the substance generated at the processing, and to execute the processing and the information acquisition while cooling such trap means.

The present invention is advantageously applicable to a case where the sample to be processed is a substance susceptible to heat, such as an organic substance, particularly a protein or another biological substance, or a composition containing water. It is particularly preferable for a composition containing water, since the sample can be worked in a state retaining water.

Since the irradiation of the focused ion beam is executed under a reduced pressure, FIB processing of a composition containing water or highly volatile organic molecules may cause evaporation of water by the heat generated during the processing. Therefore the temperature control means provided in the present invention is highly effective.

For achieving processing and structural evaluation more precisely, it is also preferable to carry out a step of determining in advance the suitable holding temperature of processing. In such a case, a sample equivalent to the sample to be worked is employed as a reference, and is worked at various temperatures, and preferred holding temperature is determined by investigating the relation between the damage in the worked portion and the cooling temperature.

After the sample 1 is confirmed to be maintained at the evaluation temperature, the surface of the sample 1 is subjected to SIM observation under constant monitoring of the temperature of the sample 1 (step S12). In such SIM observation, there is employed a weak ion beam for observation, and the sample 1 is scanned by the ion beam from the ion beam generation unit 4 under the control by the control unit 9 on the ion beam irradiation from the ion beam generation unit 4 and on the movement of the sample stage 13. Also in synchronization with such scanning, the electron detector 5 detects the secondary electrons, and the control unit 9 displays a SIM image on the display unit (not shown), based on a detection signal of such secondary electrons. In this manner, the operator can observe the SIM image of the surface of the sample 1.

Then a cross section evaluating position (position subjected to cross-section evaluation) is precisely determined from the image obtained by the SIM observation of the surface of the sample 1 (SIM image displayed on the aforementioned display unit) (step S13), and thus determined cross section evaluating position is further subjected to a SIM observation with a processing beam (step S14). In such SIM observation, the sample 1 is scanned within the range of the cross section evaluating position by the ion beam from the ion beam generation unit 4 under the control by the control unit 9 on the ion beam irradiation from the ion beam generation unit 4 and on the movement of the sample stage 13. Also in synchronization with such scanning, the electron detector 5 detects the secondary electrons, and the control unit 9 displays a SIM image on the display unit (not shown), based on a detection signal of such secondary electrons. In this manner, the operator can observe the surface SIM image of the cross section evaluating position determined in the step S14. Also after the determination of the cross section evaluating position and before the SIM observation with the processing beam, if necessary, a gas is introduced from the gas introducing means 6 for depositing a protective film on the periphery of the sample 1 including a worked portion.

Then FIB processing conditions are set (step S15). In such setting of the FIB processing conditions, the area and position to be sectioned is determined on the SIM image obtained in the surface SIM observation of the step S14, and there are also set cross section processing conditions including an accelerating voltage, a beam current and a beam diameter. The cross section processing conditions include crude processing conditions and fine processing conditions, both of which are set at this state. The crude processing conditions have a beam diameter and an energy amount larger than those in the fine processing conditions. The area and position to be sectioned may be determined on the SIM obtained with the observing ion beam in the step S12, but, in consideration of precision, it is preferable to determine on the SIM image utilizing the ion beam to be employed in the actual processing.

In such processing from the surface, an ion beam is irradiated in an amount necessary for cutting onto the area and position to be sectioned determined in step S15, where the control unit 9 controls the ion beam generation unit 4 to the preset processing conditions and also controls the movement of the sample stage 13. In this operation, in order to isolate a part of the sample, including the portion necessary for evaluation, most of the periphery of the cut-out sample, seen from above, is worked deeper than the portion for evaluation, only leaving a portion which can be cut off by a minimum processing thereafter.

After the processing from the surface, the surface of the sample 1 is subjected to a SIM observation, and there is confirmed, on the image obtained by the SIM observation (SIM image), whether the processing has proceeded close to the desired position (step S17). Then the sample is inclined together with the stage (step S18), and a cross section prepared by the processing from the surface is subjected to a SIM observation with an observing beam, in order to confirm the shape of the surface (step S18).

In case the processing has not proceeded close to the desired depth, the stage is returned to the original inclination and the foregoing steps S16 to S19 are repeated.

Then FIB processing conditions from the direction of cross section are set (step S20). In such setting of the FIB processing conditions, a sectioned area and a sectioned position are determined on the SIM image obtained in the cross sectional SIM observation of the step S19, and there are also set cross section processing conditions including an accelerating voltage, a beam current and a beam diameter. Then there is executed an FIB processing from the cross sectional direction (step S21). The cross sectional direction means an angular direction different from the surface of the sample, and allowing observation of the cross section formed by the FIB processing from the sample surface. Therefore, it need not be perpendicular to the cross section surface. In such processing from the cross sectional direction, most parts are isolated from the sample, only leaving the aforementioned portion which can be cut off by a minimum processing.

Then, after the sample is inclined to the original angle (step S22), a weak beam for observation is irradiated from the surface, thereby executing a surface SIM observation of the sample 1 (step S23). Based on the surface SIM image in the step S23, the probe is moved onto a minute sample piece to be removed (step S24). Then it is confirmed that the probe is contacted with the minute piece for example by a contrast change in the SIM image, a gas is introduced by the gas introducing means 6 and an FIB beam is irradiated in a position including the contact portion between the probe and the minute piece to deposit a film, thereby adhering the probe (step S25).

Then the aforementioned portion which can be cut off by a minimum processing is cut off with a processing beam (step S26) whereby the sample piece is isolated from the sample 1 and remains in a state fixed to the probe.

In this state, since the sample including the sample piece and the probe are maintained at equivalent temperatures by the step S11, the temperature of the sample piece scarcely changes at least by the contact of the probe. If the temperature of the probe and the sample is significantly different, the temperature of the sectioned sample piece will change close to the temperature of the probe. Thus, by confirming, prior to the contact of the probe, that the temperature of the sample and the probe is almost the same, it is possible to prevent the temperature change in the sample piece.

Thereafter, the probe with the sample piece adhered thereto is moved onto the evaluating sample table 8 (step S27), then, after confirmation that the sample piece is in contact with the sample table 8, a gas is introduced from the gas introducing means 6 and an FIB beam irradiation is executed to adhere the sample piece to the sample table 8 (step S28). Thereafter a part of the probe is cutoff by an ion beam (step S29), whereby the sample piece is transferred to the sample table 8. Also, if necessary, the sample stage 13 is inclined to cause an inclination in the sample table 8, and a film deposition is executed by a gas introduction and an ion beam irradiation thereby reinforcing the adhesion between the sample piece and the sample table 8. Also in order to facilitate the adhesion and the cutting-off of the probe, the tip of the probe is not in a position perpendicular to the sample surface nor to the cross section of the sample but is inclined by a certain angle, thereby enabling a positional confirmation by the SIM image and a processing with the ion beam.

After the sample piece is adhered to the sample table 8 for evaluation as explained above, a SIM observation of the sample surface is executed by an observing beam (step S30) to confirm the adhesion in a desired position, and subsequently an FIB processing (finish processing) is executed (step S31). In the finish processing, the sample piece fixed to the sample table 8 by the process up to the step S29 is irradiated with an ion beam of an amount necessary for the finish processing, under the control by the control unit 9 on the ion beam generation unit 4 with the aforementioned finish processing conditions and on the movement of the sample stage 13. Such finish processing allows preparation of a smooth cross section suitable, for example, for an observation of a high magnification under a transmission electron microscope.

Finally a SIM observation of the sample surface (step S32) is executed, in order to obtain an evaluation sample of a desired thickness.

In case the processing has not been made to the desired thickness, the aforementioned steps S31 and S32 are repeated.

Also a cross section for the scanning electron microscope can be prepared by a finish processing of one surface.

As explained in the foregoing, the sample processing apparatus of the present embodiment can constantly maintain the sample 1 to be evaluated, the probe and the sample table 8 for evaluation at a set temperature, so that the sample 1 is not changed in the state or the shape thereof. Consequently even a sample easily damaged by processing can be exactly evaluated for a fine structure.

The cross section processing method in the foregoing embodiments is effective for analyzing, at a desired temperature, samples on various substrates such as glass including a polymer structure, microparticles, a polymer structure containing liquid crystal, a particle dispersion structure in fibrous materials or a material causing a temperature transition. It is also effective for a sample easily damaged by an ion beam.

Also the aforementioned probe moving means may be provided in plural units in the apparatus.

Embodiment 2

Figure 4:
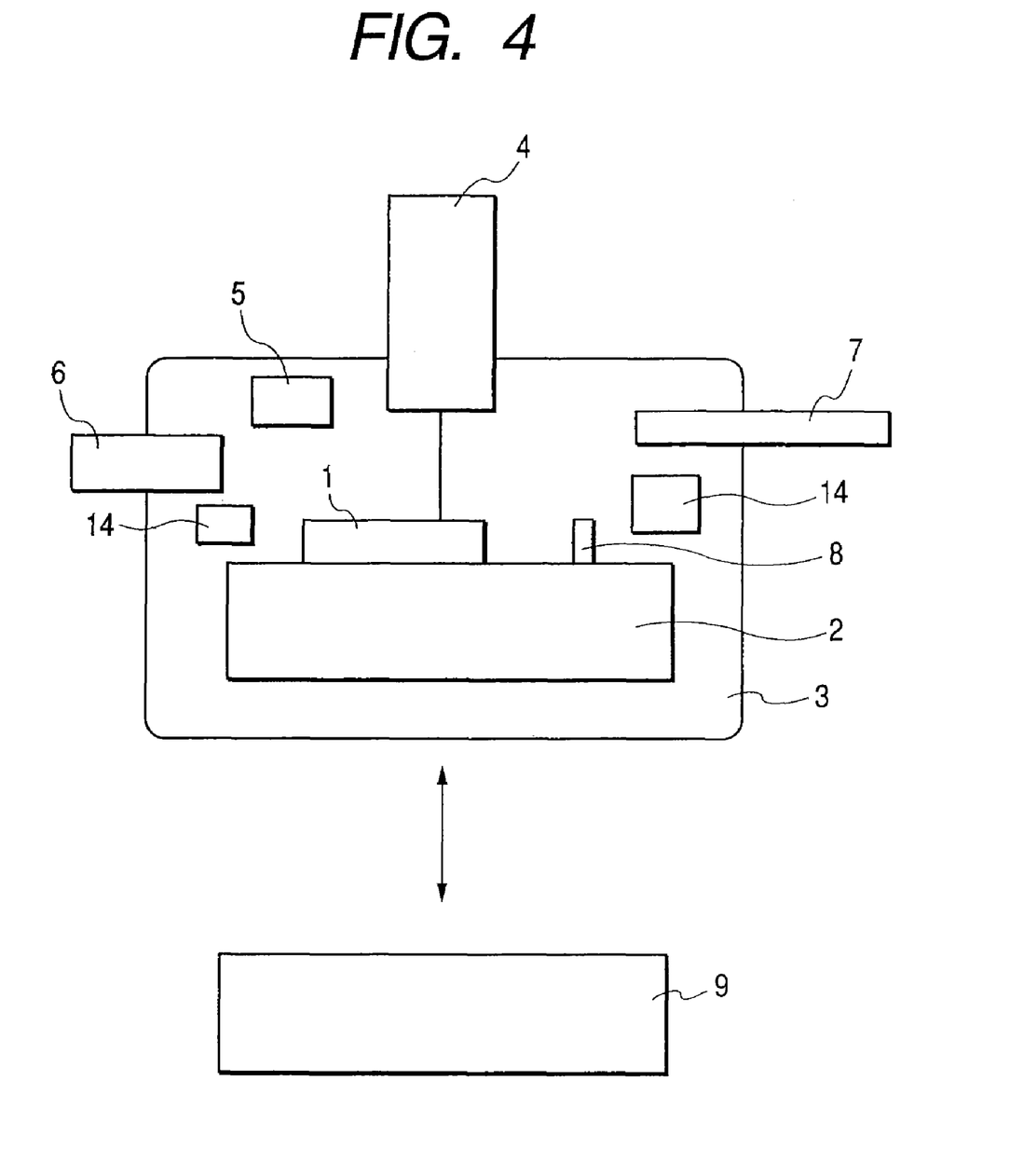
FIG. 4 is a schematic view showing a focused ion beam apparatus being an embodiment of the sample evaluation apparatus of the present invention.

In the present embodiment, in addition to the configuration of the embodiment 1, there is provided, as shown in FIG. 4, trap means 14 for preventing re-deposition of a residual gas in the sample chamber 3 or a substance generated in the processing onto the sample 1.

The trap means 14 is constituted, for example, of a metal of a satisfactory thermal conductivity, and is maintained, during the cooling of the sample 1, at a temperature equal to or lower than that of the sample 1.

The present embodiment provides an effect of preventing deposition of an impurity onto the sample 1, in case the sample 1 is worked and observed in a state maintained equal to or lower than the room temperature. For example, in case of the above-explained FIB-assisted deposition, there may result a layer of impurity between the deposition layer and the worked sample, whereby a desired function is hindered, but the present embodiment suppresses formation of such an impurity layer by the trap means 14.

The trap means 14 is provided, in a state where the sample stage supporting the sample 1, the ion beam generation unit 4, the electron detector 5, the gas introducing means 6 and the probe are positioned, in such a position as not hindering the detection system and the beam system at the processing. The trap means 14 is preferably provided in a position not hindering such detection and processing and as close as possible to the sample 1, in order to improve the trapping efficiency. Also the trap means 14 may be provided in one or more positions in the sample chamber 3 maintained at a low pressure.

Embodiment 3

In the embodiment, there will be explained a case of utilizing the apparatus of the present invention as a cross section processing apparatus in the production process of a liquid crystal display apparatus or an organic semiconductor. More specifically, there will be explained an embodiment of executing a temperature control of a sample of a relatively large area.

In case of exactly evaluating a cross sectional state in a part of a large-sized sample such as a glass substrate coated with liquid crystal, for use in a large-sized liquid crystal display apparatus, the temperature control may be executed either in a local area in the vicinity of a worked portion, or over the entire substrate. In case of temperature control of the entire substrate, a coolant pipe for passing a coolant is provided in a position of the temperature holding unit under the surface supporting the sample, thereby cooling the entire holder.

EXAMPLES

In the following, there will be explained actual examples of cross sectional evaluation of samples with the sample evaluating apparatus of the foregoing embodiments.

Example 1

In this example, there was employed a sample-processing apparatus for cross sectional observation, shown in FIG. 1. The temperature holding unit 2 was constituted of the sample stage with the temperature controller as shown in FIG. 2, incorporating a unit with a low temperature-varying system, and a cross sectional evaluation of a sample, bearing a polymer structure (polymerizable monomers HEMA, R167, HDDA polymerized together with liquid crystal) containing liquid crystal (two-frequency drivable liquid crystal DF01XX manufactured by Chisso Inc.) on a glass substrate, was executed in the following process.

The sample was fixed with a carbon paste to a unit with a low temperature-varying system, and the unit was set on the sample stage 13. The sample stage 13 with the sample was inserted in the sample chamber 3, which was then evacuated to a predetermined low pressure.

Then the evaluation temperature was set at −100° C., and it was confirmed that the sample was maintained at such evaluation temperature. A surface SIM observation was executed on an area including a cross sectional observation portion of the sample, under constant monitoring of the sample temperature. Based on an image obtained by the surface SIM observation, an approximately central portion of the sample was determined as a cross sectional observation portion.

Then the determined cross sectional observation portion was irradiated with an ion beam to acquire a SIM image. The ion beam in this operation was a very weak one of the observation mode. More specifically, there were employed a gallium ion source, an acceleration voltage of 30 kV, a beam current of 20 pA and a beam diameter of about 30 nm. A cross section processing position was designated on the acquired SIM image.

Then the designated cross section processing position was subjected to an FIB processing (surface processing).

Figure 5A:
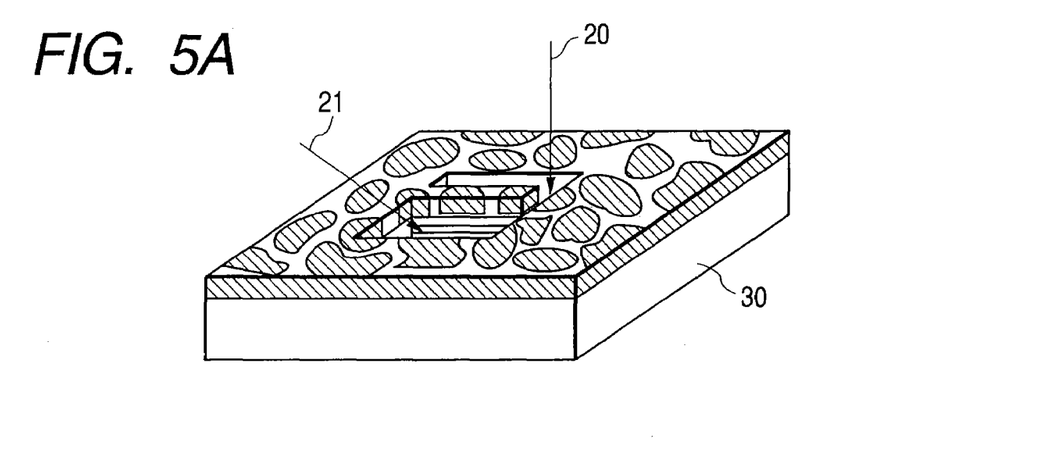
FIG. 5A is a schematic view showing sample piece preparation by FIB processing from two directions.

More specifically, there were employed an acceleration voltage of 30 kV, a beam current of 50 pA and a beam diameter of 300 nm to form, in the cross sectional processing position, a rectangular recess of a square shape of 40 μm and a depth of 30 μm. Then an L-shaped recess was formed similarly with a processing beam so as to be connected with the rectangular recess, leaving an evaluation portion. Then the sample was inclined, and, after a confirmation of the processing to the desired position with a weak beam for SIM observation, the bottom portion of the remaining evaluation portion was subjected to an FIB processing (cross section processing). The inclining angle was about 60°. FIG. 5A is a schematic view of the sample prepared by such FIB processing. At an approximate center of a sample 30, there were formed, by the irradiation of the ion beam 20 and by the following ion beam irradiation with the inclination of the sample, a rectangular recess, an L-shaped recess connected to the rectangular recess and a slat-shaped sample piece of which bottom is detached by an ion beam 21 after the inclination of the sample and which is partially connected to the sample.

Figure 5B:
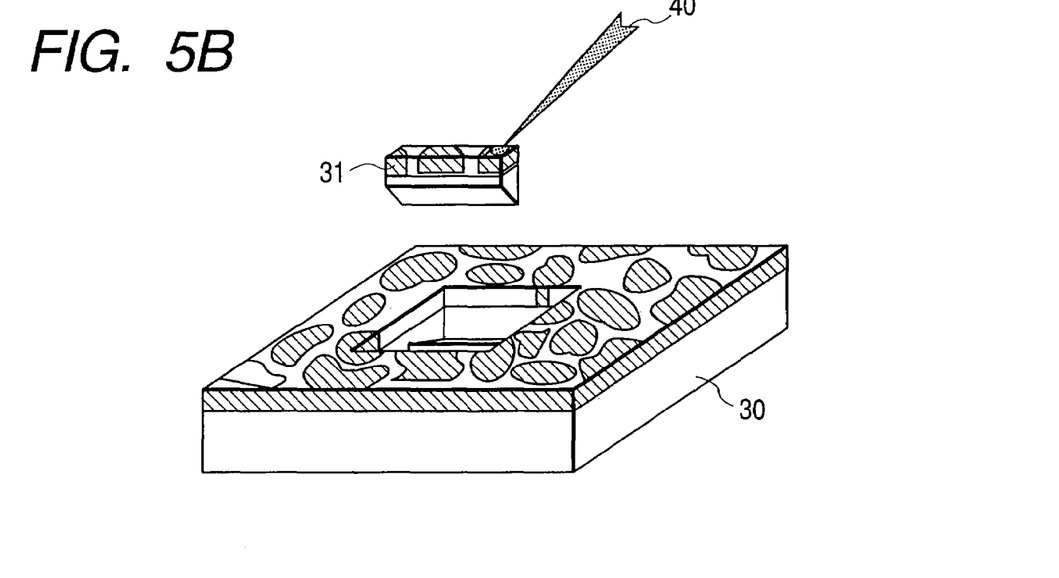
FIG. 5B is a schematic view showing a sectioned sample piece.

Then the inclined sample was returned to the original state, then the probe was contacted with the sample piece partially connected to the sample, and a film was formed in the contact position of the probe and the sample piece by introducing a gas from the gas introducing means and executing an FIB beam irradiation, thereby adhering the probe to the sample piece. Thereafter the partial connecting portion between the sample piece and the sample was FIB processed to cut off the sample piece from the sample, and the probe was elevated to lift the sample piece together with the probe. FIG. 5B is a schematic view showing thus sectioned sample piece. The sample piece partially connected to the sample 30 as shown in FIG. 5A was adhered to the probe 40, then separated from the sample 30 by cutting off the connecting portion, and was lifted as a sample piece 31. In this operation, it was confirmed that the probe was maintained at a temperature of about −100° C., the same as that of the sample. For film formation, there was employed a gas of tungsten carbonyl ($W(CO)_6$).

Figure 5C:
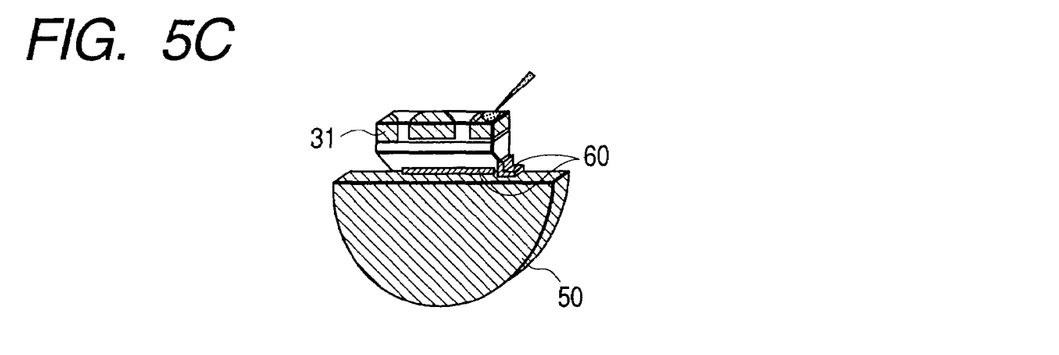
FIG. 5C is a schematic view showing the sample piece fixed to a sample table.

Then the sample piece on the probe was moved, together with the probe, onto the sample table, contacted with the sample table under temperature control and adhered to the sample table by a gas introduction as in the case of probe adhesion, and the probe used for moving the sample piece was cut off by an FIB processing. FIG. 5C is a schematic view showing the sample table on which the sample piece was adhered. The sample piece 31 was fixed by the sample table 50 by a deposition film 60.

Then a finish processing was conducted. In this case, a thin piece was prepared for TEM observation.

In such finish processing, the processing was conducted with gradually weaker conditions, and, during the processing, the sample surface under processing was SIM observed from time to time for confirming whether the processing proceeded close to the desired position. Finally, for improving the precision of cross sectional processing, the cross sectional processing portion was further worked under a weak condition similar to that in the SIM observation.

In the present example, as explained in the foregoing, the FIB processing was conducted while the sample was maintained at −100° C., so that the cross sectional processing could be executed without deforming of the liquid crystal layer during the processing. After a thin slice for TEM was prepared in this manner, the sample was returned to the normal temperature and was TEM observed, whereby a cross section of the polymer layer structure on the substrate could be observed.

Example 2

In the present example, a cross sectional evaluation of polymer particles (polystyrene) prepared on a PET substrate was executed in the following procedure.

Figure 6A:
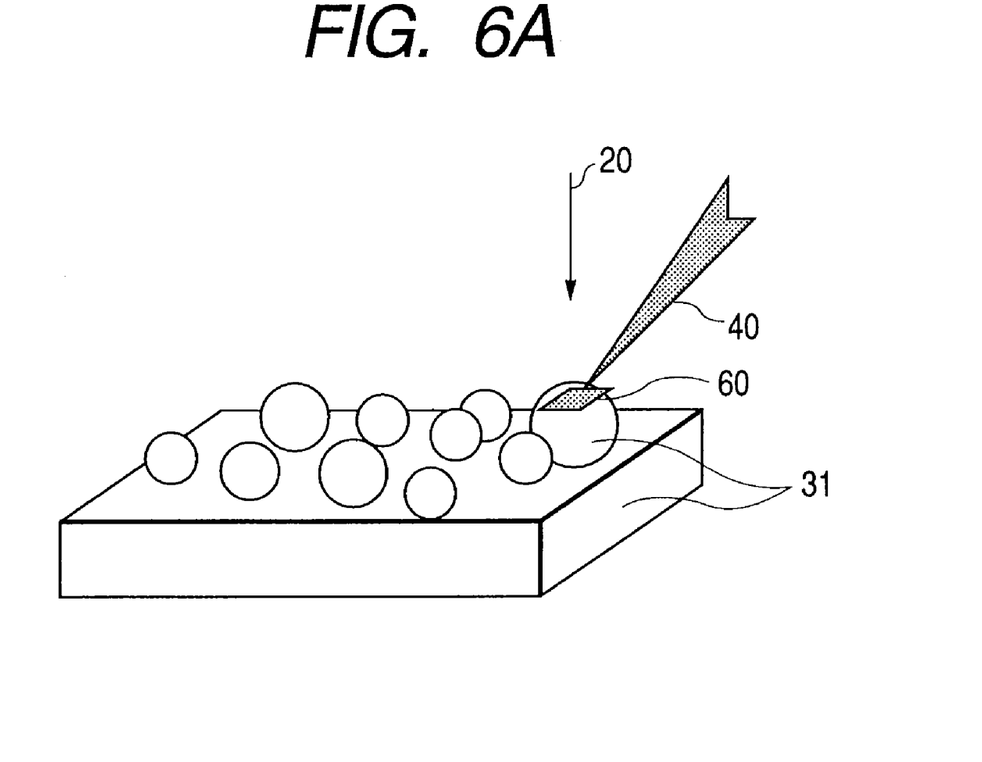
FIG. 6A is a schematic view showing a probe attached to a part of a sample.
Figure 6B:
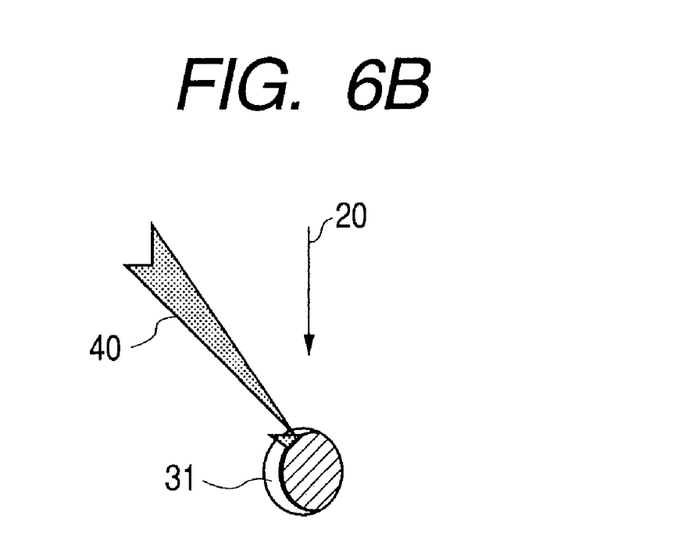
FIG. 6B is a schematic view showing a sample attached to the probe and cross-sectioned by FIB processing.

The apparatus shown in FIG. 1 was set at a temperature of about 10° C., and the sample and the probe were temperature controlled. After the tip of the probe was contacted with the polymer particle to be evaluated as in Example 1, and the polymer particle and the probe were adhered by a gas introduction and an FIB irradiation. FIG. 6A is a schematic view showing the probe 40 and the sample 31 thus adhered, and a deposition film 60. Then the polymer particle was moved together with the probe, and FIB processing was executed at the cross sectional observation portion. FIG. 6B is a schematic view showing the probe 40 and the sample 31 after the cross sectional processing.

After cross sectional processing of the polymer particle in this manner, the sample was taken out together with the probe and was subjected to a cross sectional SEM observation and an elemental analysis in another evaluation apparatus. At first the SEM observation proved that the polymer particle had a uniform interior without a bubble. There were employed conditions of an acceleration voltage of 15 kV and a magnification up to about 30,000.

Then, during the SEM observation, specific X-ray emitted from the cross section of the sample 31 was acquired to prepare a mapped image (elemental analysis), thereby proving that aluminum was dispersed in the polymer.

In the foregoing there has been explained a method of evaluating a cross section of a sample, but the present invention is not limited thereto. For example, the present invention includes a configuration where a substance deposited to the surface is removed, thereby exposing the surface to be observed and executing a surface observation.

The invention claimed is:

1. A sample processing apparatus comprising:
   a stage for supporting a sample;
   first temperature control means for controlling a temperature of said sample;
   ion beam generation means for irradiating said sample with an ion beam;
   detection means for detecting a signal emitted from said sample in response to the irradiation of said ion beam;
   a probe for obtaining a part of the sample processed by the irradiation of said ion beam and conveying it to a sample table;
   second temperature control means for controlling a temperature of said probe; and
   third temperature control means for controlling a temperature of said sample table.

2. The sample processing apparatus according to claim 1, wherein
   the ion beam generated by said ion beam generation means is used to expose a face to be acquired and said detection means is used to acquire information under conditions that the temperature of said sample is regulated to a predetermined temperature by said first temperature control means; and
   section and attachment of the sample are carried out in a state where the temperature of said probe and sample is adjusted to a predetermined temperature by said first and second temperature control means.

3. The sample processing apparatus according to claim 1, wherein said first and second temperature control means are provided with cooling means for cooling said sample to a temperature equal to or lower than a room temperature.

4. The sample processing apparatus according to claim 1, wherein said stage, said ion beam generation means, said detection means, said probe and said sample table are provided in a chamber with a controllable atmosphere, and said apparatus further comprises trap means for trapping a gas remaining in said chamber.

5. The sample processing apparatus according to claim 1, wherein said first temperature control means includes a temperature-varying system in a portion onto which said sample is fixed; and the apparatus further includes:
   a sample stage enabling moving or inclining of the sample fixed thereon;
   a probe stage having a movable tip;
   a sample table for evaluation;
   first temperature detection means which is mounted in a part of said temperature-varying system to detect the temperature in the vicinity of the sample fixed to said temperature-varying system; and
   temperature control means for controlling temperature of said temperature-varying system on the basis of the temperature detected by said first temperature detection means, thereby maintaining said sample at a predetermined temperature.

6. A sample processing apparatus according to claim 5, wherein an ion beam can be irradiated on a lateral surface of the sample held on said temperature-varying system.

7. A sample processing apparatus according to claim 5, wherein said temperature control means further includes second temperature detection means for directly detecting the temperature of the sample; and display means for displaying the temperature detected by said second temperature detection means.

8. A sample processing apparatus according to claim 7, wherein said temperature control means executes temperature control in said temperature-varying system on the basis of the temperatures detected by said first and second temperature detection means.

9. A sample processing apparatus according to claim 1, wherein said emitted signal is a secondary electron or secondary ion.

* * * * *